US00PP36603P2

(12) United States Plant Patent
Monte-Michielsen

(10) Patent No.: US PP36,603 P2
(45) Date of Patent: Apr. 15, 2025

(54) GERANIUM PLANT NAMED 'TOSPL200522'

(50) Latin Name: ***Pelargonium* interspecific**
Varietal Denomination: TOSPL200522

(71) Applicant: Ball Horticultural Company, West Chicago, IL (US)

(72) Inventor: Fabienne Monte-Michielsen, Tinte (NL)

(73) Assignee: BALL HORTICULTURAL COMPANY, West Chicago, IL (US)

( * ) Notice: Subject to any disclaimer, the term of this patent is extended or adjusted under 35 U.S.C. 154(b) by 0 days.

(21) Appl. No.: 18/917,877

(22) Filed: Oct. 16, 2024

(51) Int. Cl.
*A01H 5/02* (2018.01)
*A01H 6/42* (2018.01)

(52) U.S. Cl.
USPC ..... Plt./324

(58) Field of Classification Search
USPC ..... Plt./263.1, 324
See application file for complete search history.

(56) References Cited

U.S. PATENT DOCUMENTS

PP29,542 P3 * 7/2018 Snijder ..... A01H 5/02
Plt./324

* cited by examiner

*Primary Examiner* — Karen M Redden
(74) *Attorney, Agent, or Firm* — C. Anne Whealy

(57) ABSTRACT

A new and distinct interspecific Geranium plant named 'TOSPL200522', characterized by its broadly upright and mounding plant habit; moderately vigorous growth habit; freely basal branching habit; dark green-colored velvety leaves; early and freely flowering habit; and semi-double type flowers with medium red-colored petals that are held above the foliar plane on strong peduncles.

2 Drawing Sheets

Figure 1:
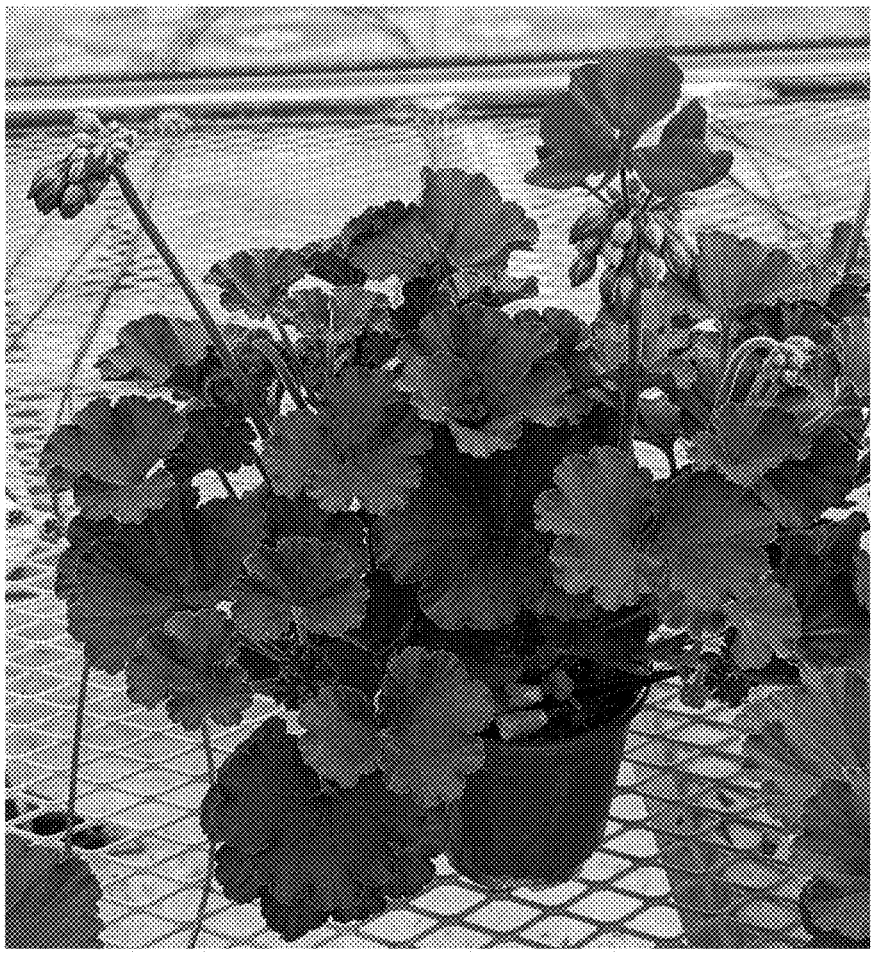

Botanical designation: *Pelargonium* interspecific.
Cultivar denomination: 'TOSPL200522'.

BACKGROUND OF THE INVENTION

The present invention relates to a new and distinct cultivar of interspecific Geranium plant, botanically known as *Pelargonium* interspecific, and hereinafter referred to by the cultivar name 'TOSPL200522'.

The new interspecific Geranium plant is a product of a planned breeding program conducted by the Inventor in Hendrik-Ido-Ambacht, The Netherlands. The objective of the breeding program is to develop new upright to mounded and moderately vigorous interspecific Geranium plants that have dark green-colored leaves, flower for a long period of time and are high temperature-tolerant.

The new interspecific Geranium plant originated from a cross-pollination made by the Inventor in Hendrik-Ido-Ambacht, The Netherlands in September 2019 of a proprietary selection of *Pelargonium* interspecific identified as code number TE0157, not patented, as the female, or seed, parent with *Pelargonium* interspecific 'TOSTC4011', not patented, as the male, or pollen, parent. The new interspecific Geranium plant was discovered and selected by the Inventor as a single flowering plant from within the progeny of the stated mass cross-pollination in a controlled greenhouse environment in Hendrik-Ido-Ambacht, The Netherlands in July 2020.

Asexual reproduction of the new interspecific Geranium plant by vegetative terminal cuttings in a controlled greenhouse environment in Hendrik-Ido-Ambacht, The Netherlands since July 2020 has shown that the unique features of this new interspecific Geranium plant are stable and reproduced true to type in successive generations.

SUMMARY OF THE INVENTION

Plants of the new interspecific Geranium have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'TOSPL200522'. These characteristics in combination distinguish 'TOSPL200522' as a new and distinct interspecific Geranium plant:

1. Broadly upright and mounding plant habit.
2. Moderately vigorous growth habit.
3. Freely basal branching habit.
4. Dark green-colored velvety leaves.
5. Early and freely flowering habit.
6. Semi-double type flowers with medium red-colored petals that are held above the foliar plane on strong peduncles.

Plants of the new interspecific Geranium differ primarily from plants of the female parent selection in flower petal color as flower petals of plants of the new interspecific Geranium are medium red in color whereas flower petals of plants of the female parent selection are red purple in color. In addition, plants of the new interspecific Geranium are more outwardly spreading than and not as upright as plants of the female parent selection.

Plants of the new interspecific Geranium differ primarily from plants of the male parent, 'TOSTC4011', in flower petal color as flower petals of plants of the new interspecific Geranium are medium red in color whereas flower petals of plants of 'TOSC4011' are darker red in color. In addition, plants of the new interspecific Geranium have fewer petals per flower than plants of 'TOSC4011'.

Plants of the new interspecific Geranium can be compared to plants of the *Pelargonium* interspecific 'PEQZ0028', disclosed in U.S. Plant Pat. No. 29,542. In side-by-side comparisons, plants of the new interspecific Geranium differ from plants of 'PEQZ0028' in the following characteristics:

1. Plants of the new interspecific Geranium are more uniformly mounded than plants of 'PEQZ0028'.
2. Leaves of plants of the new interspecific Geranium are darker green in color than leaves of plants of 'PEQZ0028'.
3. Leaves of plants of the new interspecific Geranium do not have a distinct zonation pattern whereas leaves of plants of 'PEQZ0028' have a distinct zonation pattern.
4. Flowers of plants of the new interspecific Geranium are darker red in color than flowers of plants of 'PEQZ0028'.

BRIEF DESCRIPTION OF THE PHOTOGRAPHS

The accompanying colored photographs illustrate the overall appearance of the new interspecific Geranium plant showing the colors as true as it is reasonably possible to obtain in colored reproductions of this type. Colors in the photographs may differ slightly from the color values cited in the detailed botanical description which accurately describe the colors of the new interspecific Geranium plant.

The photograph on the first sheet (FIG. 1) is a side perspective view of a typical flowering plant of 'TOSPL200522' grown in a container.

Figure 2:
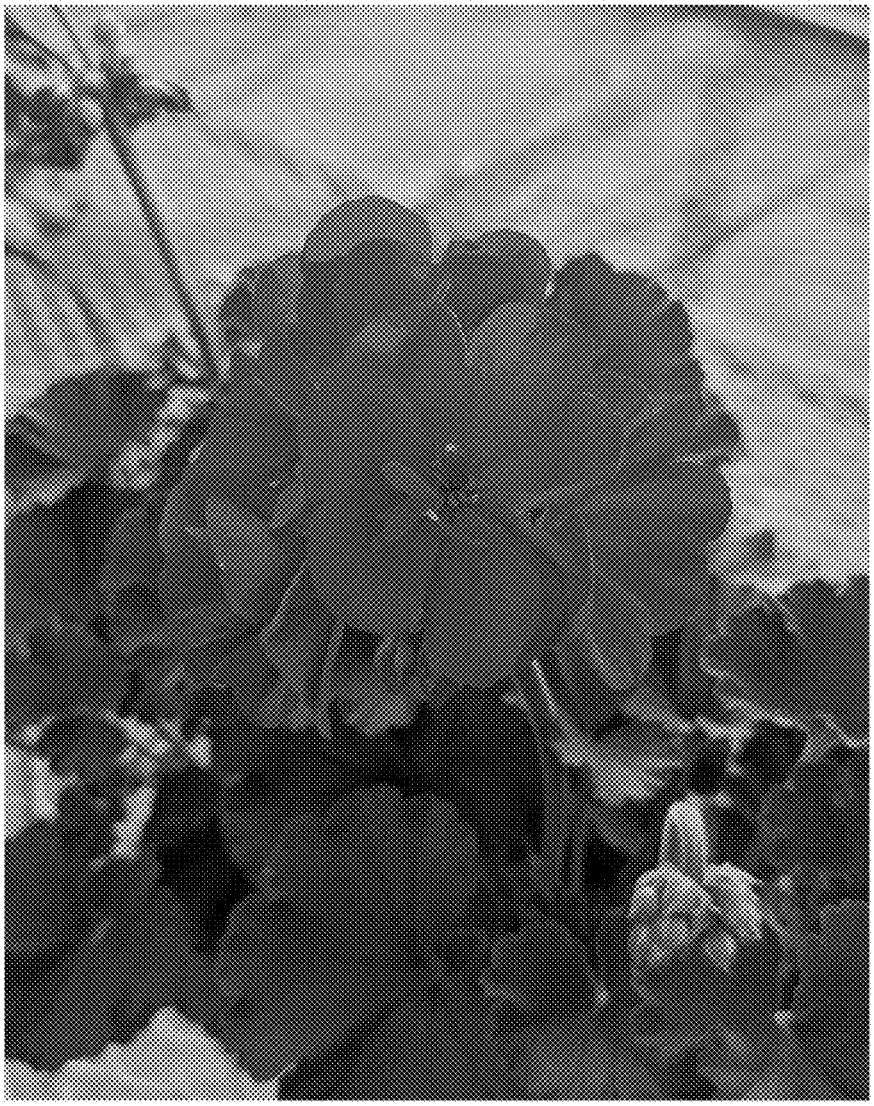

The photograph on the second sheet (FIG. 2) is a close-up view of a typical flowering plant of 'TOSPL200522'.

DETAILED BOTANICAL DESCRIPTION

The aforementioned photographs and following observations, measurements and values describe plants grown in 10.5-cm containers during the spring in a polyethylene-covered greenhouse in Arroyo Grande, California and under cultural practices typical of commercial interspecific Geranium production. During the production of the plants, day temperatures averaged 20° C. and night temperatures averaged 18° C. Plants were 18 weeks old when the photographs and the detailed description were taken. In the detailed description, color references are made to The Royal Horticultural Society Colour Chart, 1995 Edition, except where general terms of ordinary dictionary significance are used.

Botanical classification: *Pelargonium* interspecific 'TOSPL200522'.

Parentage:

*Female, or seed, parent.*—Proprietary selection of *Pelargonium* interspecific identified as code number TE0157, not patented.

*Male or pollen parent.*—*Pelargonium* interspecific 'TOSTC4011', not patented.

Propagation:

*Type.*—By vegetative terminal cuttings.

*Time to initiate roots.*—About nine to twelve days

*Time to produce a rooted young plant.*—About three to four weeks.

*Root description.*—Fine, fibrous; typically white in color, actual color of the roots is dependent on substrate composition, water quality, fertilizers, substrate temperature and age of roots.

*Rooting habit.*—Freely branching; dense.

Plant description:

*Plant and growth habit.*—Broadly upright and mounding plant habit; overall shape, broad inverted triangle; densely foliated; moderately vigorous growth habit and moderate growth rate; freely basal branching habit with about six primary lateral branches each primary lateral branch with potentially two secondary lateral branches developing at every node; pinching is typically not required.

*Plant height, to top of umbels.*—About 36 cm to 38 cm.

*Plant height, to top of foliar plane.*—About 24 cm to 26 cm.

*Plant width.*—About 33 cm by 36 cm.

*Lateral branches.*—Length: About 20 cm to 22 cm. Diameter: About 8 mm to 10 mm. Internode length: About 2 cm to 2.3 cm. Strength: Strong, not flexible. Texture and luster: Moderately pubescent; semi-glossy. Color: Close to 144A, becoming closer to 146A with development.

Leaf description:

*Arrangement.*—Alternate; simple.

*Length.*—About 6 cm to 6.75 cm.

*Width.*—About 7.5 cm to 8.5 cm.

*Shape.*—Rounded cordate.

*Apex.*—Rounded.

*Base.*—Cordate, open.

*Margin.*—Crenate with shallow and divergent indentations.

*Venation pattern.*—Palmate.

*Texture and luster, upper and lower surfaces.*—Pubescent; velvety; slightly glossy.

*Color.*—Developing and fully expanded leaves, upper surface: Close to 147A; venation, close to 147A; no discernible zonal pattern. Developing and fully expanded leaves, lower surface: Close to 147B; venation, close to 147C.

*Petioles.*—Length: About 5 cm to 7 cm. Diameter: About 3 mm to 4 mm. Strength: Moderately strong, flexible. Texture and luster, upper and lower surfaces: Pubescent; slightly glossy. Color, upper and lower surfaces: Close to 146A.

Flower description:

*Flower arrangement and flowering habit.*—Semi-double type flowers arranged in hemispherical umbels arising from apical leaf axils; umbels displayed above the foliar plane on strong peduncles; flowers face upright to outwardly depending on the position on the umbel; freely flowering habit with about 20 to 24 developing and open flowers per umbel and numerous umbels developing per plant during the flowering season.

*Fragrance.*—None detected.

*Flowering season.*—Early flowering habit; plants begin flowering about eight to nine weeks after planting rooted young plants; in the garden in California, flowering begins in April and continues until frost in the autumn.

*Flower longevity*.—Depending on temperature, flowers last about six to ten days on the plant; umbels last about three to four weeks on the plant; flowers persistent.

*Umbel height*.—About 6.5 cm.

*Umbel diameter*.—About 11 cm.

*Flower diameter*.—About 4.75 cm by 4.75 cm.

*Flower depth* (*height*).—About 2.4 cm.

*Flower buds*.—Length: About 1 cm. Diameter: About 5 mm. Shape: Ovoid. Texture and luster: Slightly pubescent; matte. Color: Close to 146A to 146B.

*Petals*.—Quantity per flower: About five; petals imbricate. Length, upper petals: About 2.5 cm. Length, lower petals: About 2.4 cm. Width, upper petal: About 2 cm. Width, lower petals: About 2.25 cm. Shape: Obovate. Apex: Rounded. Base: Cuneate. Margin: Entire; slightly undulate. Texture and luster, upper and lower surfaces: Smooth, glabrous; velvety; slightly glossy. Color: When opening and fully opened, upper surface: Close to N45B to N45C; venation, close to N45B to N45C; color does not change with subsequent development. When opening and fully opened, lower surface: Close to 46B; venation, close to 46B; color does not change with subsequent development.

*Petaloids*.—Quantity per flower: About five to eight; petaloid imbricate; petaloids vary in size and shape. Length: About 5 mm to 15 mm. Width: About 1.5 mm to 3 mm. Shape: Roughly obovate. Apex: Rounded to slightly acute. Base: Cuneate. Margin: Entire; slightly undulate. Texture and luster, upper and lower surfaces: Smooth, glabrous; velvety; slightly glossy. Color: When opening and fully opened, upper surface: Close to N45B to N45C; venation, close to N45B to N45C; color does not change with subsequent development. When opening and fully opened, lower surface: Close to 46B; venation, close to 46B; color does not change with subsequent development.

*Sepals*.—Calyx length: About 1.25 cm. Calyx diameter: About 2 cm. Quantity per flower: Five arranged in a single whorl. Length: About 1.25 cm. Width: About 2 mm to 4 mm. Shape: Lanceolate. Apex: Acute. Base: Truncate. Margin: Entire. Texture and luster, upper surface: Smooth, glabrous; semi-glossy. Texture and luster, lower surface: Pubescent; semi-glossy. Color, upper and lower surfaces: Close to 146A.

*Peduncles* (*umbel stems*).—Length: About 17 cm to 18 cm. Diameter: About 4 mm to 5 mm. Strength: Strong; flexible. Angle: Mostly upright to slightly outwardly. Texture and luster: Pubescent; semi-glossy. Color: Close to 146A to 146B variably overlain with close to 165A.

*Pedicels* (*individual flower stems*).—Length: About 1.5 cm to 2 cm. Diameter: About 1 mm. Strength: Moderately strong; flexible, wiry. Texture and luster: Pubescent; semi-glossy. Color: Close to 165A variably overlain with close to 165A.

*Reproductive organs*.—Androecium: Stamen quantity per flower: About eight to ten. Filament length: About 4 mm. Filament color: Close to 155D. Anther size: About 1 mm by 2 mm. Anther shape: Tubular. Anther color: Close to 58A. Pollen amount: None observed. Gynoecium: Pistil quantity per flower: One. Pistil length: About 7 mm. Stigma diameter: About 2.5 mm. Stigma shape: Five-parted. Stigma color: Close to 58A. Style length: About 2.5 mm. Style color: Close to 58A. Ovary color: Close to 144A. Seeds and fruits: To date, seed and fruit development have not been observed on plants of the new interspecific Geranium.

Pathogen & pest resistance: To date, plants of the new interspecific Geranium have not been observed to be resistant to pathogens and pests common to interspecific Geraniums.

Temperature tolerance: Plants of the new interspecific Geranium have been observed to tolerate temperatures ranging from about 1° C. to about 40° C.

It is claimed:

1. A new and distinct interspecific Geranium plant named 'TOSPL200522' as herein illustrated and described.

* * * * *